US012642688B2

(12) United States Patent
Brown

(10) Patent No.: US 12,642,688 B2
(45) Date of Patent: Jun. 2, 2026

(54) OSTOMY POCKET PATCH

(71) Applicant: Adam's Ostomy Pocket, LLC,
Loveland, OH (US)

(72) Inventor: Margaret A. Brown, Loveland, OH
(US)

(73) Assignee: ADAM'S OSTOMY POCKET, LLC,
Loveland, OH (US)

( * ) Notice: Subject to any disclaimer, the term of this
patent is extended or adjusted under 35
U.S.C. 154(b) by 0 days.

(21) Appl. No.: 19/361,293

(22) Filed: Oct. 17, 2025

(65) Prior Publication Data

US 2026/0124065 A1 May 7, 2026

Related U.S. Application Data

(60) Provisional application No. 63/715,579, filed on Nov.
3, 2024.

(51) Int. Cl.
*A41D 13/12* (2006.01)
*A61F 5/449* (2006.01)
*A61F 5/44* (2006.01)

(52) U.S. Cl.
CPC .................................... *A61F 5/449* (2013.01)

(58) Field of Classification Search
CPC ........................................................ A61F 5/449
See application file for complete search history.

(56) References Cited

U.S. PATENT DOCUMENTS

| | | | |
|---|---|---|---|
| 4,266,300 A | | 5/1981 | Partridge |
| 4,495,662 A | * | 1/1985 | Miller ................ A41D 13/1254 |
| | | | 2/919 |
| 4,656,673 A | | 4/1987 | Easton et al. |
| 4,705,512 A | | 11/1987 | Faucher |
| 4,846,820 A | * | 7/1989 | Jensen .................... A61F 5/445 |
| | | | 604/339 |
| 4,888,006 A | | 12/1989 | Beaupied |
| 4,941,869 A | * | 7/1990 | D'Amico ................ A61F 5/445 |
| | | | 604/277 |
| 5,051,259 A | * | 9/1991 | Olsen .................. A61F 13/0213 |
| | | | 428/355 R |
| 5,142,702 A | | 9/1992 | Piloian |
| 5,248,308 A | | 9/1993 | von Emster |
| 5,380,309 A | * | 1/1995 | Keyes .................... A61F 5/448 |
| | | | 604/338 |

(Continued)

*Primary Examiner* — Robert H Muromoto, Jr.

(74) *Attorney, Agent, or Firm* — Ronald J. Richter;
Nesbitt IP LLC

(57) ABSTRACT

A patch for attachment within a shirt or blouse can form a
pocket which can accommodate expansion of a concealed
ostomy bag. The patch includes a curved middle seam which
allows the pocket to expand towards the wearer's skin.
Oversized, rounded welts are located adjacent to the pocket
opening to protect the patch from peeling off of the garment
over time. The patch is intended to be attached to the inside
surface of the garment in order to form a definitive pocket
which can receive and support an expanding ostomy bag
close to the body, and can allow the garment to lie substan-
tially flat against the wearer's body without creating an
awkward silhouette. The patch has a substantially triangular,
symmetrical shape, which allows it to be rotated prior to
attachment, for example, to fit either the right or left corner
of a shirt or blouse.

7 Claims, 4 Drawing Sheets

(56) References Cited

U.S. PATENT DOCUMENTS

| | | | |
|---|---|---|---|
| 5,401,264 A * | 3/1995 | Leise, Jr. | A61F 5/441 604/333 |
| 5,429,625 A * | 7/1995 | Holmberg | A61F 5/448 604/338 |
| 5,465,425 A | 11/1995 | Crispin | |
| 5,496,296 A * | 3/1996 | Holmberg | A61F 5/443 604/336 |
| 5,499,403 A | 3/1996 | Harrigan | |
| 5,607,412 A | 3/1997 | Brown | |
| 5,607,413 A * | 3/1997 | Holmberg | A61F 5/448 604/338 |
| 5,626,570 A * | 5/1997 | Gallo | A61F 5/449 604/345 |
| 5,722,965 A * | 3/1998 | Kuczynski | A61F 5/443 604/338 |
| 5,809,576 A | 9/1998 | Huston et al. | |
| 5,865,819 A * | 2/1999 | Cisko, Jr. | A61F 5/445 604/338 |
| 6,023,790 A | 2/2000 | Schwartz | |
| 6,202,222 B1 * | 3/2001 | Robbins | A41D 13/1254 2/400 |
| 6,709,421 B1 * | 3/2004 | Falconer | A61F 5/441 604/335 |
| 8,439,883 B1 * | 5/2013 | Johnsen | A61F 5/448 604/338 |
| 8,708,987 B2 * | 4/2014 | Cramer | A61F 5/443 604/344 |
| 9,271,874 B2 * | 3/2016 | Luce | A61F 13/82 |
| 9,498,372 B2 * | 11/2016 | Fattman | A61F 5/448 |
| 11,071,640 B2 * | 7/2021 | Fattman | A61F 5/4404 |
| 11,148,845 B1 * | 10/2021 | Ellis | A61F 5/445 |
| 12,376,984 B2 * | 8/2025 | Stroebech | A61F 5/4404 |
| 2003/0153882 A1 * | 8/2003 | Mandzij | A61F 5/4407 604/339 |
| 2003/0168068 A1 * | 9/2003 | Poole | A61B 1/00156 128/850 |
| 2003/0204174 A1 * | 10/2003 | Cisko, Jr. | A61F 5/443 604/338 |
| 2004/0006320 A1 * | 1/2004 | Buglino | A61F 5/443 604/344 |
| 2004/0087920 A1 * | 5/2004 | Etheredge, III | A61F 5/443 604/332 |
| 2004/0193122 A1 * | 9/2004 | Cline | A61F 5/445 604/332 |
| 2005/0113770 A1 * | 5/2005 | Pedersen | B32B 3/02 604/332 |
| 2005/0143696 A1 * | 6/2005 | Pedersen | A61F 5/448 604/332 |
| 2005/0177119 A1 * | 8/2005 | Tsai | A61F 5/448 604/332 |
| 2007/0123832 A1 * | 5/2007 | Cline | A61F 5/445 604/335 |
| 2008/0033379 A1 * | 2/2008 | Pedersen | A61F 5/4407 604/335 |
| 2008/0312615 A1 | 12/2008 | Hunter | |
| 2009/0082743 A1 * | 3/2009 | Buglino | A61F 5/4405 604/335 |
| 2010/0114044 A1 * | 5/2010 | Cramer | A61F 5/448 604/332 |
| 2010/0114045 A1 * | 5/2010 | Cramer | A61F 5/445 604/338 |
| 2010/0174256 A1 * | 7/2010 | Rosengren | A61F 5/445 604/344 |
| 2010/0205720 A1 | 8/2010 | Ortega Astor | |
| 2010/0249734 A1 * | 9/2010 | Strang | A61F 5/449 604/345 |
| 2011/0213322 A1 * | 9/2011 | Cramer | A61F 5/443 604/332 |
| 2012/0283678 A1 * | 11/2012 | Nguyen-DeMary | A61F 5/445 604/338 |
| 2013/0304008 A1 * | 11/2013 | Hanuka | A61F 5/445 604/338 |
| 2014/0200536 A1 * | 7/2014 | Nassopoulos | A61F 5/445 604/338 |
| 2015/0065971 A1 * | 3/2015 | Goldsmith | A61F 5/448 604/342 |
| 2015/0320585 A1 * | 11/2015 | Fattman | A61F 5/4404 604/344 |
| 2016/0074206 A1 * | 3/2016 | Nassopoulos | A61F 5/445 604/338 |
| 2020/0030134 A1 * | 1/2020 | Hopper | A61F 5/448 |
| 2020/0078206 A1 * | 3/2020 | Chiladakis | A61F 5/449 |
| 2020/0214371 A1 * | 7/2020 | Apelt | A61F 5/449 |
| 2020/0253777 A1 * | 8/2020 | Jones | A61F 5/443 |
| 2020/0337885 A1 * | 10/2020 | Donovan | A61F 5/448 |
| 2021/0056363 A1 * | 2/2021 | Song | G06V 20/695 |
| 2021/0369484 A1 * | 12/2021 | Holden | A61F 5/441 |
| 2021/0369485 A1 * | 12/2021 | Evans | A61F 5/445 |
| 2021/0369491 A1 * | 12/2021 | Holden | A61F 5/445 |
| 2021/0369493 A1 * | 12/2021 | Young | A61F 5/4407 |
| 2021/0369494 A1 * | 12/2021 | Holden | A61F 5/448 |
| 2022/0087851 A1 * | 3/2022 | Stroebech | A61B 5/6833 |
| 2023/0240883 A1 | 8/2023 | Apelt | |
| 2024/0082046 A1 * | 3/2024 | Holden | A61F 5/445 |
| 2024/0091049 A1 * | 3/2024 | Young | A61F 5/445 |
| 2024/0252344 A1 * | 8/2024 | Hill | A61F 5/4404 |
| 2024/0307212 A1 * | 9/2024 | Evans | A61F 5/445 |
| 2025/0044242 A1 * | 2/2025 | Mahnashi | A61B 5/14532 |
| 2025/0127649 A1 * | 4/2025 | Lee | A61F 5/445 |
| 2025/0332020 A1 * | 10/2025 | Stroebech | A61F 5/445 |

* cited by examiner

OSTOMY POCKET PATCH

CROSS REFERENCES TO RELATED APPLICATION

The present application claims the benefit of U.S. Provisional Application No. 63/715,579 filed Nov. 3, 2024, the entire disclosure of which is incorporated herein by reference.

FIELD OF THE INVENTION

The present invention relates in general to ostomy bags, and in particular to a patch that is attachable to the inside of a patient's shirt or other garment to create a pocket for receiving and supporting an ostomy bag.

BACKGROUND OF THE INVENTION

An ostomy bag or pouch is a medical device configured to collect waste. Ostomy bags are commonly associated with colostomies and ileostomies, which are surgeries that bypass diseased parts of the bowel and allow the body to get rid of waste products. With a colostomy, a surgeon will create an opening from the large intestine through the abdomen for waste to pass through. An ileostomy is similar, but the opening connects to the small intestine. For patients who have had a cystectomy (bladder removal) due to cancer or trauma, a urostomy may be necessary to redirect urine into a urostomy bag. In each case, the opening or passageway made through the abdomen is called a stoma, and the ostomy bag typically has a flange or fitting at the upper part of the bag for removable attachment to the stoma, creating an airtight seal. There are a variety of ostomy bags in common use, and they are typically made of a transparent or semi-transparent plastic material. The bottom of the collection bag can also include a drain tube that can be opened to release fluid wastes.

Patients first learning to live with an ostomy bag can find it difficult to feel comfortable going out in public. In addition, the plastic material can stick to and irritate the patient's skin, and the bag itself can be somewhat cold to the touch when attached, and then warm as it fills, which can be rather uncomfortable. While ostomy bag design has improved over the years to improve physical comfort, patients still find that the profile of the ostomy bag is noticeable under their clothing, and they worry about bulging or otherwise showing in public. Furthermore, as the ostomy bag fills with waste, the weight of the pouch increases and may provide stress on the stoma.

Holders and pouches for supporting ostomy bags are known, and can range from full garments to belts and vests with pockets, as well as reversibly attachable pockets. Nevertheless, such holders tend to be heavy and bulky, do not allow the patient to wear their "every day" clothing, and have generally been insufficient in providing ample support and comfort, or providing a form-fitting ability. Typical pockets for holding and supporting ostomy bags can be either disposable and/or washable/reusable, can be made of any type of fabric, such as cloth, canvas, leather, plastic, or any other suitable material, and they typically are reversibly attachable with Velcro, buttons, zippers, snaps, or hooks.

While many types of ostomy bag holders and supports are known, there is an ongoing need for pocket for an ostomy bag having a simple design that is economical to make and easy to employ, that can be attached to any garment, and can reduce the discomfort associated with wearing an ostomy bag. It would also be beneficial to provide a pocket for supporting an ostomy bag that can allow the garment to hug close to the body, without hanging out or bulging as the ostomy bag expands.

SUMMARY OF THE INVENTION

The present invention provides a pocket configured for permanent attachment to a garment, such as a shirt or blouse, to receive and support an ostomy bag close to the body.

Specifically, in accordance with a first aspect of the invention, the present invention provides a patch for attachment to an inside surface of a garment to create a definitive pocket for receiving and supporting an ostomy bag, the patch comprising: (a) a first half-patch; and (b) a second half-patch, wherein the first half-patch and the second half-patch are identical, each including an angled corner, a curved side, a straight side, a base side, a welt, and a stitch line, wherein the angled corner and the curved side of the first half-patch are sewn to the angled corner and the curved side of the second half-patch to create a bottom corner and a middle seam for the patch, wherein the patch is adapted for attachment to the inside surface of a garment to create a definitive pocket, the definitive pocket having an opening for receiving and holding an ostomy bag, wherein the welts are adjacent to either end of the opening, and wherein the middle seam allows the definitive pocket to expand in the horizontal direction towards a wearer's body as the ostomy bag fills.

While the nature and advantages of the present invention will be more fully appreciated from the following drawings and detailed description, showing the contemplated novel combinations and elements as herein described, and more particularly defined by the appended claims, it is understood that changes in the precise embodiments of the present invention are meant to be included within the scope of the claims.

BRIEF DESCRIPTION OF THE DRAWINGS

The accompanying drawings illustrate embodiments of the invention and, together with a general description given above and the detailed description given below, serve to explain the principles of the invention.

DETAILED DESCRIPTION OF THE INVENTION

The inventive ostomy pocket patch described herein is concealed within a garment and can accommodate expansion of an ostomy bag. The patch is intended for permanent attachment to the inside surface of the garment, such as a shirt or blouse, in order to form a "definitive" pocket on the inside surface of the garment, which can receive and support the ostomy bag close to the body. So long as the ostomy bag is emptied regularly to avoid overfilling, the pocket created by patch allows the garment's fabric to lie substantially flat against the wearer's body as the ostomy bag expands, without creating an awkward silhouette.

Figure 1:
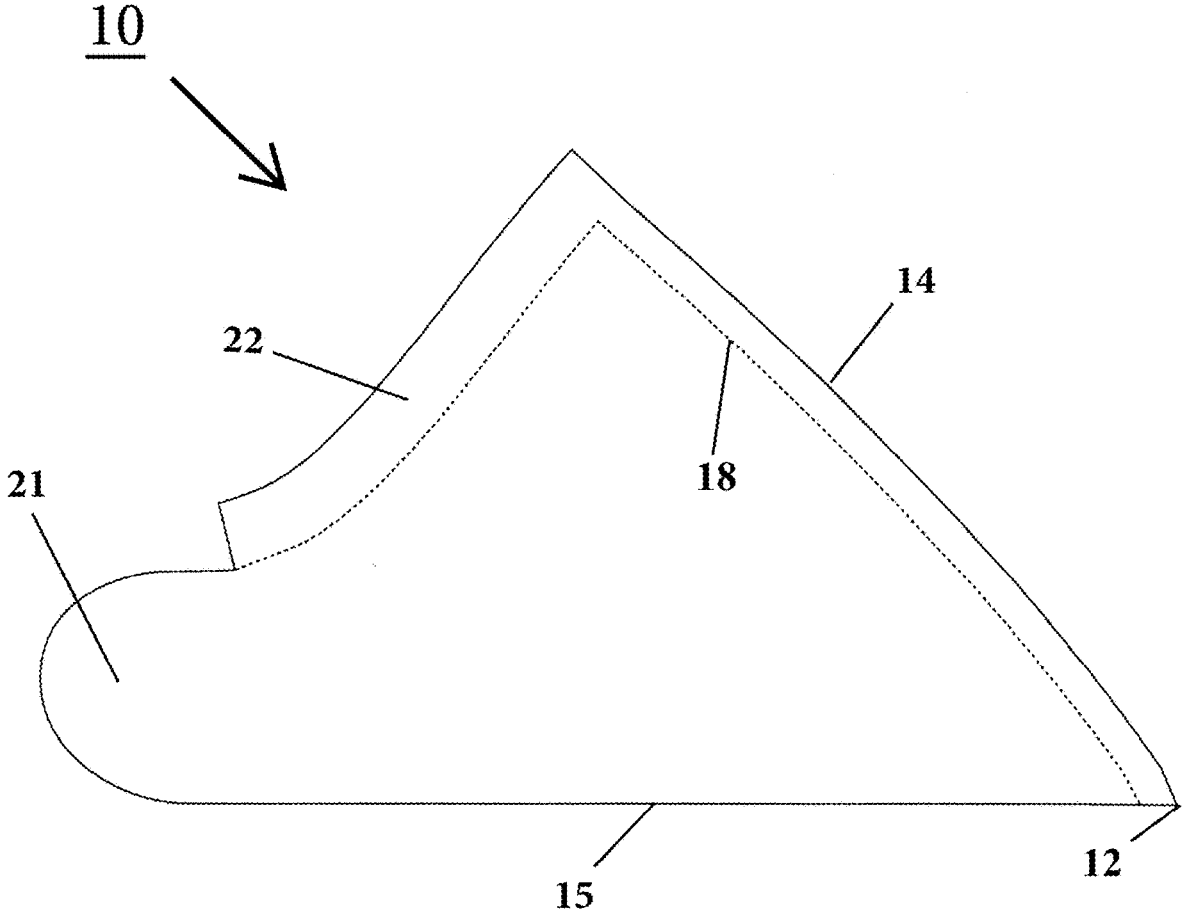
FIG. 1 is a perspective view of a half-patch for the pocket patch according to the present invention.
Figure 2:
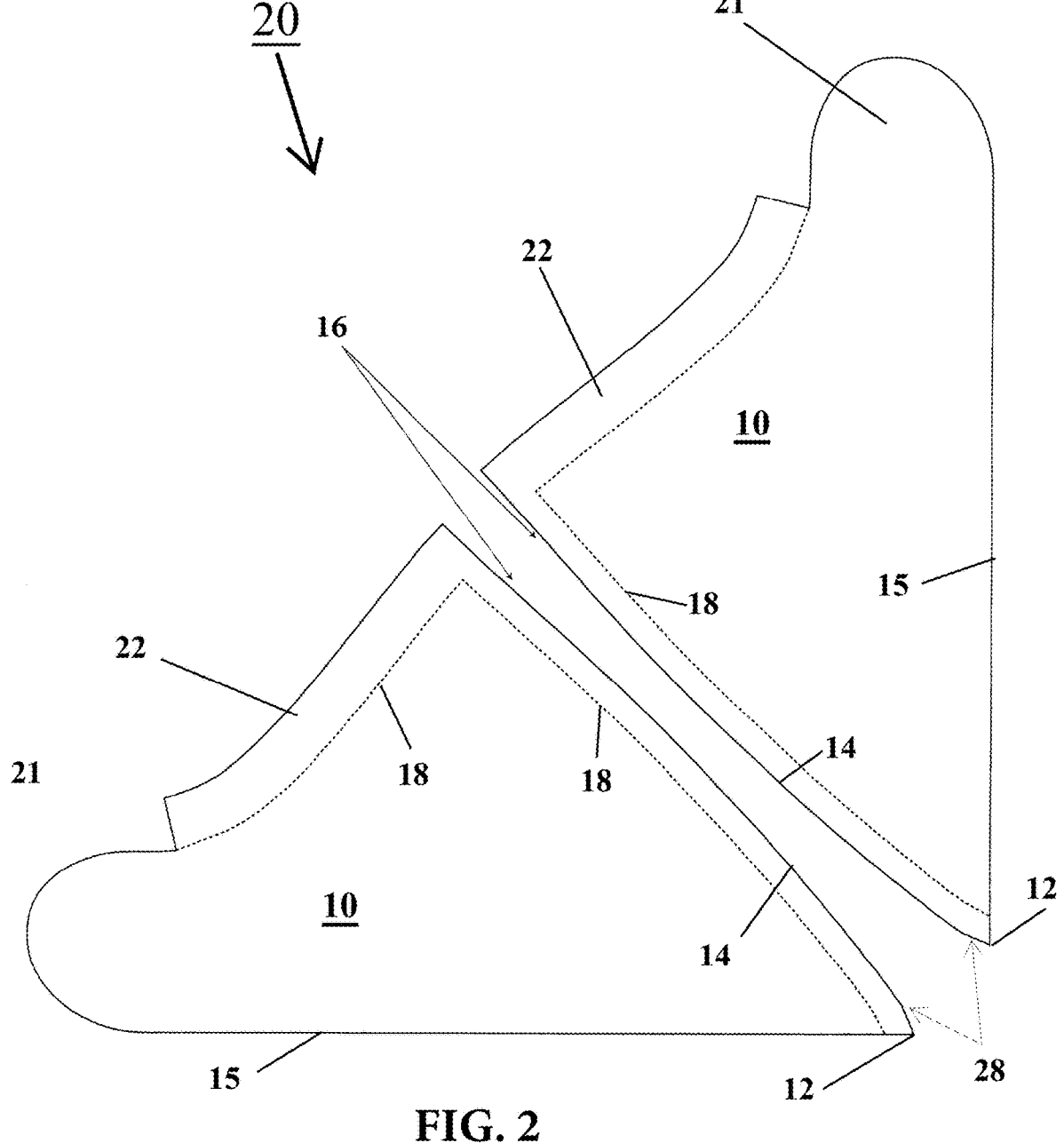
FIG. 2 illustrates two half-patches as shown in FIG. 1, prior to them being sewn together to form a pocket patch.

With reference to FIGS. 1-4, aspects of the inventive pocket patch 20 for receiving and supporting an ostomy bag close to the body are illustrated. FIG. 1 shows a half-patch 10 used to create the inventive pocket patch 20, in which each half-patch 10 includes an angled corner 12, a curved side 14, a straight side 15, a base side 22, a welt 21, and a stitch line 18 (dashed line). As illustrated in FIG. 2, two pieces of fabric, each shaped as the half-patch 10 shown in FIG. 1, can be arranged so that the angled corner 12 of each half-patch is aligned with the other, and the curved side 14 of each half-patch is aligned with the other. The corners 12 and curved sides 14 of each half-patch can then be sewn or hemmed together along the stitch line 18, and thereafter their base sides 22 can be hemmed along the stitch line 18 to create the opening 24 for the pocket.

Figures 3A, 3B:
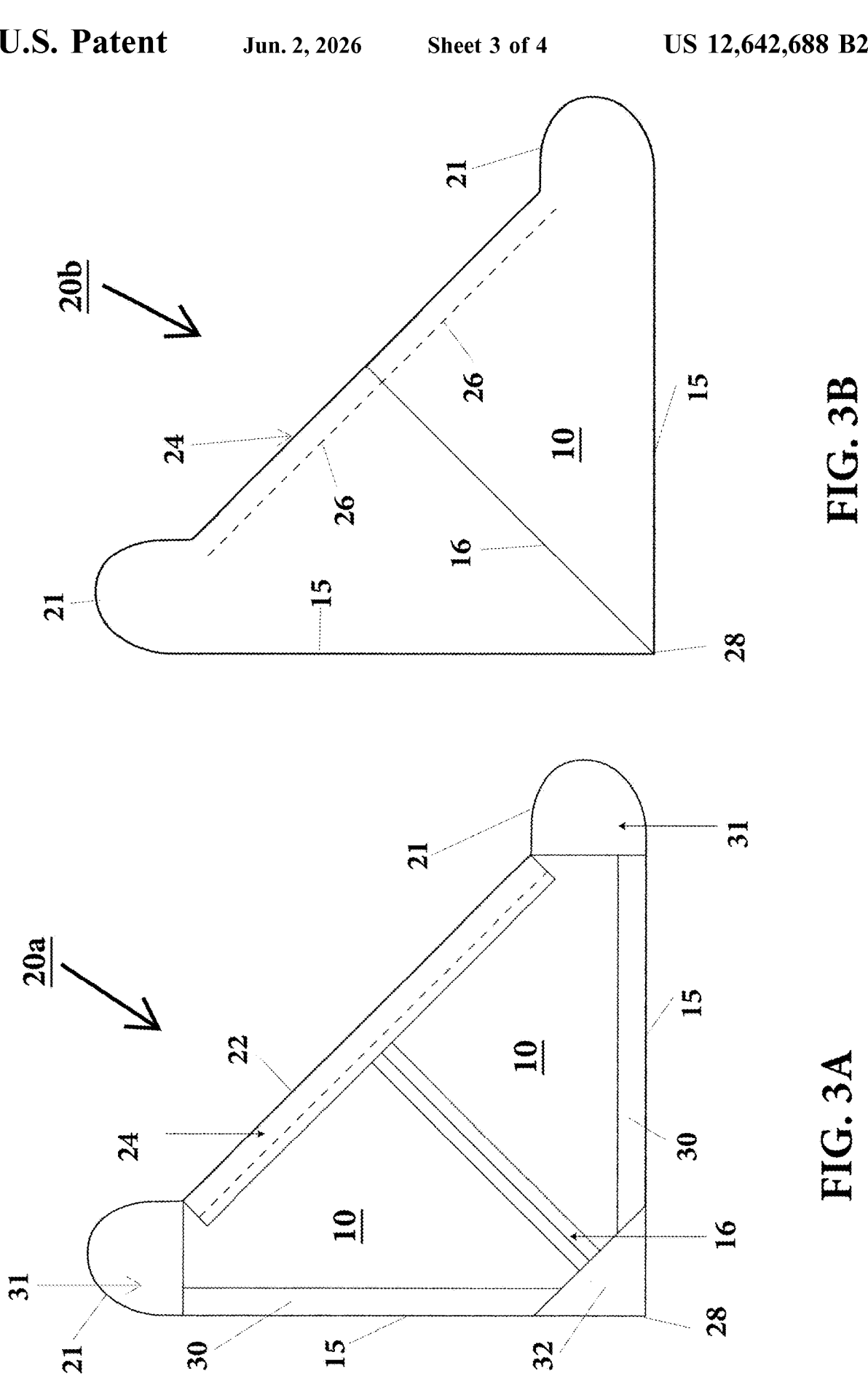
FIG. 3A is the "inside" surface of the pocket patch formed from sewing together the two half-patches shown in FIG. 2.
FIG. 3B is the "outside" surface of the pocket patch formed from sewing together the two half-patches shown in FIG. 2.
Figures 4A, 4B:
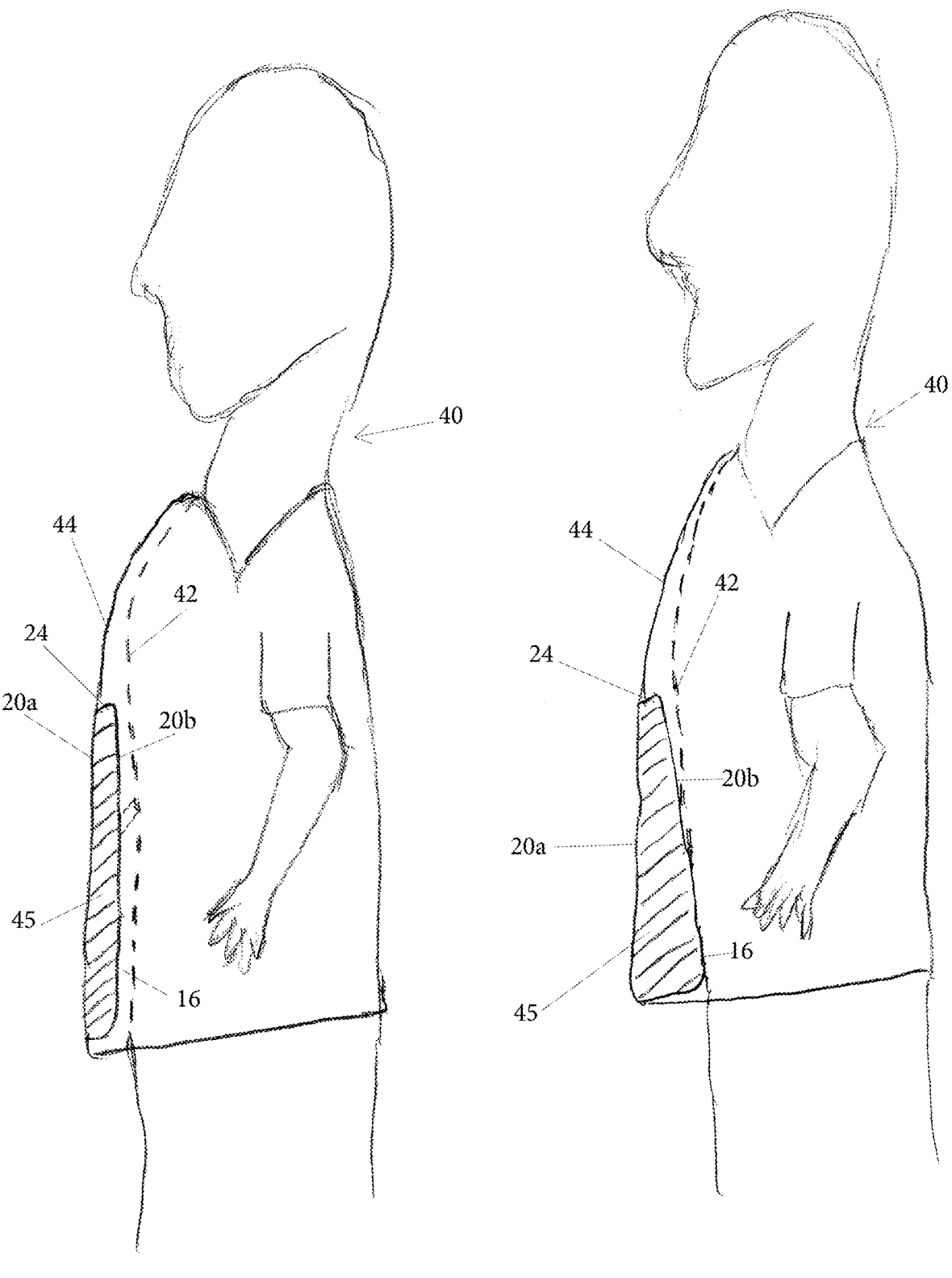
FIG. 4A shows the pocket patch being worn by a user with the ostomy bag empty.
FIG. 4B shows the pocket patch of FIG. 4A as the ostomy bag fills and expands.

The stitch line 18 provides dimension to the definitive pocket (45, see FIGS. 4a and 4B) upon the patch 20 being ironed on or otherwise attached to the inside surface of a garment, according to the invention, so that the definitive pocket bows open slightly, even when empty, and also allows for inward expansion, i.e., toward the users skin (see FIGS. 4A and 4B). In addition, as illustrated in FIGS. 3A and 3B, the hemmed curved sides 14 form a middle seam 16 upon sewing the half-patches 10 together, and the hemmed angled corners 12 form a bottom corner 28 of the completed pocket patch 20, the fully formed pocket patch 20 preferably has a symmetrical appearance, substantially in the shape of an isosceles triangle, giving it the ability to be rotated and arranged to fit within the lower corner of either the right or the left front sides of a shirt or blouse prior to attachment, for example, of the bottom corner 28 of the pocket patch 20 to the right or left front corner of the garment. The welts 21 adjacent either end of the pocket opening 24 are preferably oversized and rounded as illustrated, making them useful for protecting the patch from peeling off of the garment over time, or over extended use or stretching of the pocket opening 24. In addition, attaching the straight sides 15 and the corner 28 of the pocket patch 20 to the end seams of the garment itself can provide additional support to help prevent sagging as the ostomy bag fills.

The inventive pocket patch 20 described above is preferably an iron-on, permanently attachable patch for adhesion to the inside surface of a garment, such as a favorite shirt or blouse; however, as noted above it must first be attached to the garment in order to create a "definitive" pocket which completes the opening 24 for holding an ostomy bag. See FIG. 3A, which illustrates the "back" panel 20a of the pocket patch 20, or the future "inside" surface 20a, which includes the addition of medium-weight, double-sided adhesive strips 30, 31, 32. These adhesive strips are preferred for attaching the straight sides 15, the welts 21 and the bottom corner 28 of the patch to the inside surface of the user's garment, so that once the patch 20 is applied to the garment, the definitive pocket 45 (see FIGS. 4A and 4B), is formed which includes a completed opening 24 for holding an ostomy bag. As seen in FIG. 3A, the medium-weight, double-sided adhesive strips 30, 31, 32 include straight tape 30 attached over each straight side 15 of the patch 20, welt tape 31 attached over each of the welts 21, and corner tape 32 attached over the bottom corner 28 of the patch 20. However, it is noted that there is no adhesive strip attached to the base side 22 of the patch, so that the opening 24 of the definitive pocket 45 can be formed for receiving the ostomy bag. The adhesive strips are preferably made of a very thin, lightweight layer of film or webbing, for example, tape marketed by the Plantion company. The use of medium-weight, double-sided adhesive is preferred because it is a non-woven, heat-activated bonding material which acts as a heat-activated glue for permanently joining the inside surface 20a to the user's garment without the need for sewing.

FIG. 3B illustrates the "front" panel 20b of the pocket patch, which is the future "outside" surface 20b of the definitive pocket 45 (see FIGS. 4A and 4B), which will face the wearer's skin after attachment. As illustrated, the front panel includes the middle seam 16, which bows in towards the wearer in use, due to the hemmed curved sides 14 of each half-patch 10. It can be appreciated that the front panel 20b is symmetrical, and substantially in the shape of an isosceles triangle, with the straight sides 15 of each half-patch 10 forming the legs of the triangle, and the connected base sides 22 of each half-patch forming the base of the isosceles triangle. The welts 21 provide oversized corners which aid in the stability of the pocket patch's attachment to the user's garment.

The opening 24 of the pocket, in addition to being protected by the oversized welts 21 on either side from overuse or the from the repeated stretching caused by expanding ostomy bags, also includes a hem 26, which may or may not be elasticized. In one embodiment, the opening 24 can include an elasticized hem 26 (see, e.g., FIGS. 3A and 3B) which can help to secure the ostomy bag within the pocket, when either empty or filled. When the ostomy bag is empty, the elasticized hem 26 can snugly hold the ostomy bag in place. As the ostomy bag fills, the elastic's tension can loosen, but still help to secure the enlarging bag and prevent it from shifting or bulging away from the body. This can also allow the ostomy bag to move in unison with the wearer's body, adjusting to the bag's size and creating a "custom" fit. This is particularly useful for active individuals, as it maintains security and comfort during movement.

As best seen in FIGS. 3A and 3B, creation of the middle seam 16 preferably employs a "301 single needle stitch". The 301 stitch is done by passing a single needle thread through the fabric and interlocking it with a bobbin thread at the center of the material, forming a "lockstitch". It is the preferred stitch for joining the two half-patches 10, and is formed by placing the two pieces of fabric directly on top of one another (i.e., superimposing them) and sewing them together near their curved sides 14, along line 18. Also, the base sides 22 of each half-patch 10 are hemmed along the stitch line 18 to create the opening 24 for the definitive pocket 45 (see FIGS. 4A and 4B). The interlocking threads create a strong, tight, and secure seam which is low-bulk, and can provide a smooth feel to the seam that looks the same on both sides. This stitch is preferred due to its durability, smooth appearance, and versatility.

Although the preferred use of iron-on adhesive tape makes the inventive pocket patch permanent, and thus not removable or reusable, this attachment method is preferred because the iron-on tape provides a stronger holding power, lighter weight, and an invisible finish as compared to reusable attachment means known in the art, such as hook-and-loop fasteners (Velcro), clips, buttons, or buckles. Since the preferred iron-on adhesive tape is physically light in weight, the "medium-weight" designation is used in the tape industry to refer to the strength of the bond it creates, which is a stronger, more permanent hold than "light weight" fusible adhesives which are used for more fragile materials such as chiffon or lace. Advantageously, medium-weight double-sided adhesive tape creates a smooth bond with the garment, without bulky seams or stitches, and heat activation only requires a household iron to melt the adhesive and bond the fabrics together.

In a preferred embodiment, due to the curvature of the middle seam 16, the hemmed pocket patch 20 expands towards the surface on which it lies, and not the surface to which it is attached. For example, as can be appreciated from viewing FIGS. 4A and 4B, a side view of the definitive pocket 45 is illustrated in which the back panel or inside surface 20*a* of the patch is attached to the inside surface of a shirt 44 of a wearer 40. The front panel or outside surface 20*b* of the pocket patch can be seen bulging towards the skin surface 42 (dashed line) of the wearer 40. Comparing FIG. 4A to FIG. 4B, it can be appreciated that the middle seam 16 causes the pocket 45 to bow or expand towards the skin surface 42 as the ostomy bag fills and expands. Without this curved middle seam 16, the pocket would expand horizontally in both directions, i.e., both inward towards the skin surface 24 as well as outward, causing a bulge in the silhouette of the wearer's shirt 44. This curved middle seam 16 can thus be useful for allowing inconspicuous expansion of a filling ostomy bag, allowing the pocket 45 to expand towards the wearer's body as the ostomy bag fills and expands, such that the garment does not bulge, "pouch out" or look uneven while being worn. This can also decrease the amount of downward sagging of the garment while still supporting the weight of the filling ostomy bag. The expanding curved seam 16 also allows for progressive filling of the ostomy bag without causing leaks as the bag fills, since the bag is not overly compressed or constricted. When the pocket patch 20 is attached to the front right or front left corner of a shirt or blouse, the gentle curve of the seam 16 may also conform to the body's natural contours, reducing irritation and creating a more discreet profile.

The inventive pocket patch can be used for both adult and children's clothing, and it's overall size can be adjusted to create larger or smaller pockets, as needed according to the specific user and the specific type/size of ostomy bag being supported. While the inventive pocket patch is preferably for use with ostomy bags, it is envisioned that it may also be useful for surgical drains. It will be appreciated from the foregoing description that the claimed ostomy pocket patch is simple in construction and can be quickly and easily attached to most shirts or blouses, or other garments.

While the present invention has been illustrated by the description of embodiments and examples thereof, it is not intended to restrict or in any way limit the scope of the appended claims to such detail. Additional advantages and modifications will be readily apparent to those skilled in the art. Accordingly, departures may be made from such details without departing from the scope of the invention.

What is claimed is:

1. A patch for attachment to an inside surface of a garment to create a definitive pocket for receiving and supporting an ostomy bag, the patch comprising:
   a) a first half-patch; and
   b) a second half-patch, wherein the first half-patch and the second half-patch are identical, each including an angled corner, a curved side, a straight side, a base side, a welt, and a stitch line, wherein the angled corner and the curved side of the first half-patch are sewn to the angled corner and the curved side of the second half-patch to create a bottom corner and a middle seam for the patch,
      wherein the patch is adapted for attachment to the inside surface of a garment to create a definitive pocket, the definitive pocket having an opening for receiving and holding an ostomy bag, wherein the welts are adjacent to either end of the opening, and wherein the middle seam allows the definitive pocket to expand in the horizontal direction towards a wearer's body as the ostomy bag fills.

2. The patch of claim 1, wherein the patch has a symmetrical appearance, substantially in the shape of an isosceles triangle, for being rotated and arranged to fit within a corner of the garment prior to attachment.

3. The patch of claim 1, wherein the patch is an iron-on, permanently attachable patch for attachment to the inside surface of the garment, and wherein attachment of the patch to the garment creates the definitive pocket having an opening for holding an ostomy bag.

4. The patch of claim 1, the patch further comprising a front face and a back face, wherein the back face includes adhesive strips for attaching the straight sides, the welts and the bottom corner of the patch to the inside surface of the user's garment to create the definitive pocket.

5. The patch of claim 4, wherein the welts are oversized and rounded for protecting the patch from peeling off of the garment.

6. The patch of claim 3, wherein straight sides, the welts, and the bottom corner of the patch are ironed on to the corner seams of the garment for providing additional support to the definitive pocket as the ostomy bag fills.

7. The patch of claim 1, wherein the opening of the definitive pocket includes an elasticized hem.

* * * * *